(12) United States Patent
Solaun et al.

(10) Patent No.: US 11,937,826 B2
(45) Date of Patent: Mar. 26, 2024

(54) PROXIMAL LINK WIRE FOR PREVENTING PREMATURE IMPLANT DETACHMENT

(71) Applicant: DePuy Synthes Products, Inc., RAynham, MA (US)

(72) Inventors: Daniel Solaun, Miami, FL (US); Thomas Gallerani, Miami, FL (US); David Blumenstyk, Miami, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 17/693,516

(22) Filed: Mar. 14, 2022

(65) Prior Publication Data
US 2023/0285027 A1 Sep. 14, 2023

(51) Int. Cl.
*A61B 17/00* (2006.01)
*A61B 17/12* (2006.01)

(52) U.S. Cl.
CPC .... *A61B 17/12113* (2013.01); *A61B 17/1214* (2013.01); *A61B 2017/00862* (2013.01); *A61B 2017/1205* (2013.01)

(58) Field of Classification Search
CPC .......... A61B 17/1214; A61B 17/12113; A61B 2017/1205; A61B 2017/00862; A61B 2017/12054; A61F 2/2439; A61F 2/2427; A61F 2002/9505; A61F 2002/9511
See application file for complete search history.

(56) References Cited

U.S. PATENT DOCUMENTS

| | | |
|---|---|---|
| 2,220,203 A | 2/1939 | Branin |
| 3,429,408 A | 2/1969 | Maker et al. |
| 4,858,810 A | 8/1989 | Intlekofer et al. |
| 5,108,407 A | 4/1992 | Geremia et al. |
| 5,122,136 A | 6/1992 | Guglielmi et al. |

(Continued)

FOREIGN PATENT DOCUMENTS

| | | |
|---|---|---|
| CN | 104203341 A | 12/2014 |
| CN | 106456422 A | 2/2017 |

(Continued)

OTHER PUBLICATIONS

International Search Report and Written Opinion issued in International Patent Application No. PCT/IB2023/051733 dated May 11, 2023.

*Primary Examiner* — Kelly J Bekker
*Assistant Examiner* — Lindsey R. Rivers
(74) *Attorney, Agent, or Firm* — TROUTMAN PEPPER HAMILTON SANDERS LLP

(57) ABSTRACT

Various systems and methods of deploying an implant to a target location of a body vessel are disclosed. A delivery system can include a delivery tube and a pull tube, the pull tube at least partially disposed within a first lumen of the delivery tube. A link wire with two proximal ends can be welded to the pull tube and a distal end of the link wire can include a link wire loop. A pull wire can extend through the first lumen with a distal end positioned to secure the implant to the delivery system. The pull wire includes a proximal bend positioned around the link wire loop such that the proximal bend is positioned in a proximal direction relative to the distal end of the link wire loop by a slack length. The slack length is effective to prevent premature detachment of the implant from the delivery system.

20 Claims, 5 Drawing Sheets

(56) References Cited

U.S. PATENT DOCUMENTS

| | | |
|---|---|---|
| 5,234,437 A | 8/1993 | Sepetka |
| 5,250,071 A | 10/1993 | Palermo |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,392,791 A | 2/1995 | Nyman |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,384,407 B2 | 6/2008 | Rodriguez et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 8,926,650 B2 | 1/2015 | Que et al. |
| 8,956,381 B2 | 2/2015 | Que et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,149,676 B2 | 12/2018 | Mirigian et al. |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2 | 10/2020 | Lorenzo |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2003/0009208 A1 | 1/2003 | Snyder et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0100687 A1 | 5/2006 | Fahey et al. |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0241685 A1 | 10/2006 | Wilson et al. |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0119887 A1 | 5/2008 | Que et al. |
| 2008/0269721 A1 | 10/2008 | Balgobin et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0099592 A1 | 4/2009 | Buiser et al. |
| 2009/0312748 A1 | 12/2009 | Johnson et al. |
| 2010/0094395 A1 | 4/2010 | Kellett |
| 2010/0114017 A1 | 5/2010 | Lenker et al. |
| 2010/0206453 A1 | 8/2010 | Eeflang et al. |
| 2010/0324649 A1 | 12/2010 | Mattsson |
| 2011/0092997 A1 | 4/2011 | Kang |
| 2011/0118776 A1 | 5/2011 | Chen et al. |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0083868 A1 | 4/2012 | Shrivastava et al. |
| 2012/0172913 A1 | 7/2012 | Kurrus et al. |
| 2012/0172921 A1 | 7/2012 | Yamanaka et al. |
| 2012/0179194 A1 | 7/2012 | Wilson et al. |
| 2012/0283768 A1 | 11/2012 | Cox et al. |
| 2012/0289772 A1 | 11/2012 | O'Connell et al. |

(56) References Cited

U.S. PATENT DOCUMENTS

| | | |
|---|---|---|
| 2013/0066413 A1 | 3/2013 | Jin et al. |
| 2013/0296915 A1 | 11/2013 | Bodewadt |
| 2013/0325054 A1 | 12/2013 | Watson |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0243883 A1 | 8/2014 | Tsukashima et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |
| 2015/0025562 A1 | 1/2015 | Dinh et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalacaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1 | 11/2016 | Hebert et al. |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0078263 A1 | 3/2018 | Stoppenhagen et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0296222 A1 | 10/2018 | Hebert et al. |
| 2018/0325706 A1 | 11/2018 | Hebert et al. |
| 2019/0142565 A1 | 5/2019 | Follmer et al. |
| 2019/0159784 A1 | 5/2019 | Sananes et al. |
| 2019/0192162 A1 | 6/2019 | Lorenzo et al. |
| 2019/0231566 A1 | 8/2019 | Tassoni et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1 | 12/2020 | Montidoro et al. |
| 2021/0001082 A1 | 1/2021 | Lorenzo et al. |
| 2021/0045759 A1 | 2/2021 | Merhi et al. |
| 2021/0085498 A1* | 3/2021 | Nygaard .............. A61F 2/966 |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0338248 A1 | 11/2021 | Lorenzo et al. |
| 2021/0346002 A1 | 11/2021 | Lorenzo et al. |
| 2021/0353299 A1 | 11/2021 | Hamel et al. |

FOREIGN PATENT DOCUMENTS

| | | |
|---|---|---|
| EP | 1985244 A2 | 10/2008 |
| EP | 2498691 | 9/2012 |
| EP | 3092956 A1 | 11/2016 |
| EP | 3501427 A1 | 6/2019 |
| EP | 3799803 A1 | 4/2021 |
| EP | 3854321 A1 | 7/2021 |
| EP | 1188414 A1 | 3/2022 |
| EP | 4119065 A1 | 1/2023 |
| JP | 2006-334408 A | 12/2006 |
| JP | 2012-523943 A | 10/2012 |
| JP | 2013-78584 A | 5/2013 |
| JP | 2014-399 A | 1/2014 |
| WO | WO 2007/070793 A2 | 6/2007 |

(56) References Cited

FOREIGN PATENT DOCUMENTS

| | | |
|---|---|---|
| WO | WO 2008/064209 A1 | 5/2008 |
| WO | WO 2009/132045 A2 | 10/2009 |
| WO | WO 2012/158152 A1 | 11/2012 |
| WO | WO 2016/014985 A1 | 1/2016 |
| WO | WO 2017/066386 A1 | 4/2017 |
| WO | WO 2018/022186 A1 | 2/2018 |
| WO | WO 2020/148768 A1 | 7/2020 |

* cited by examiner

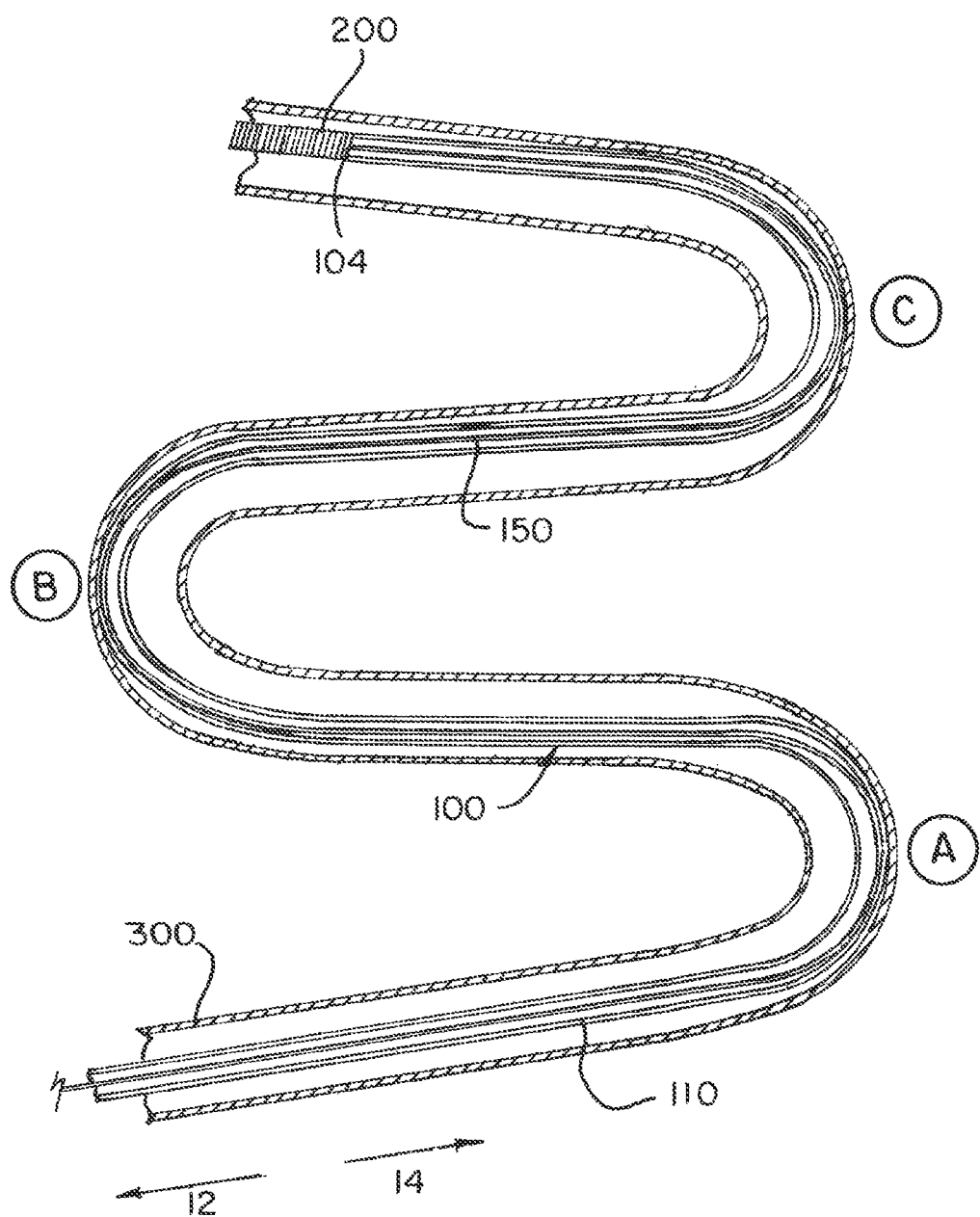

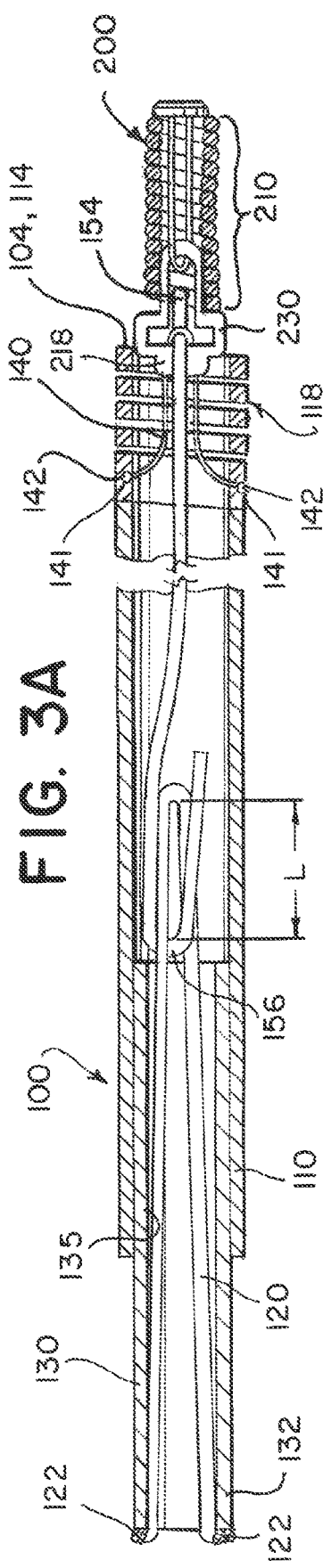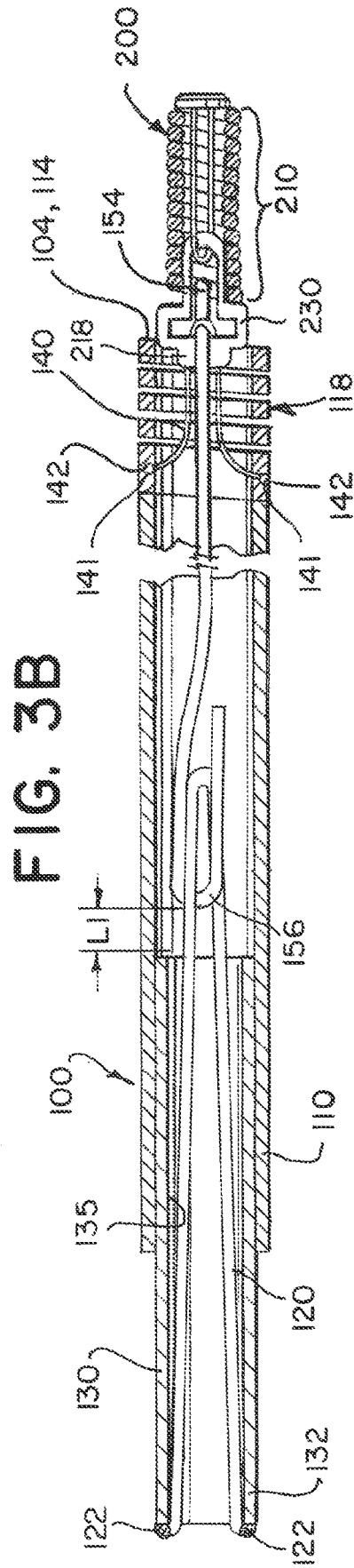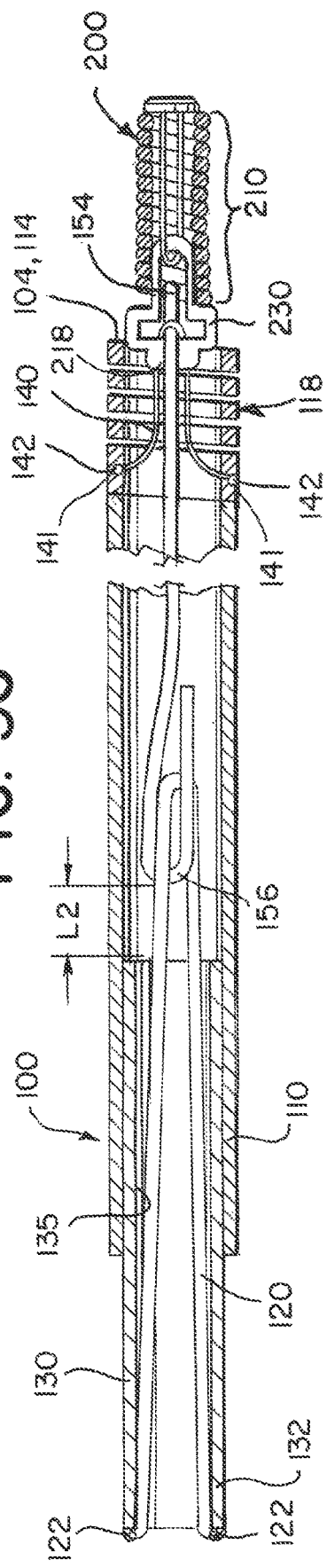

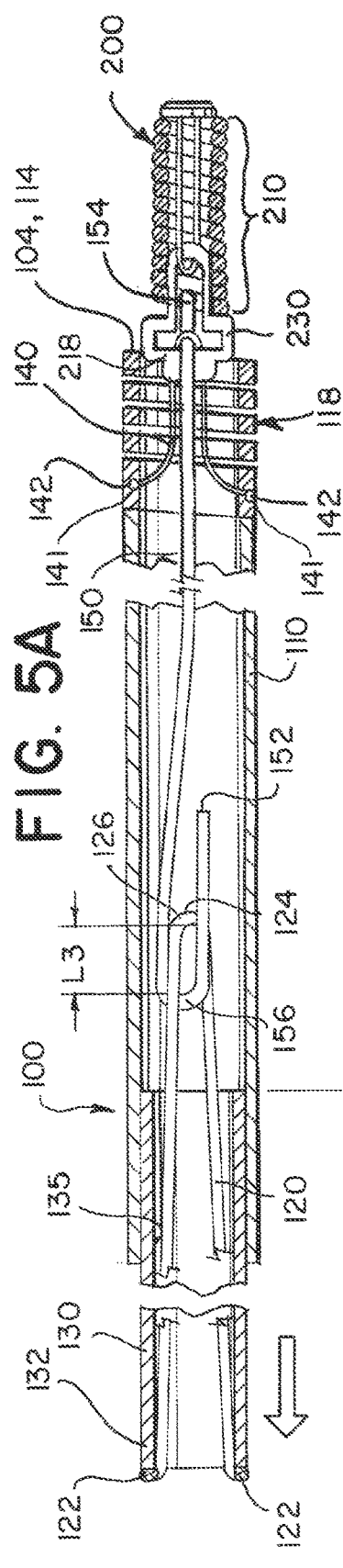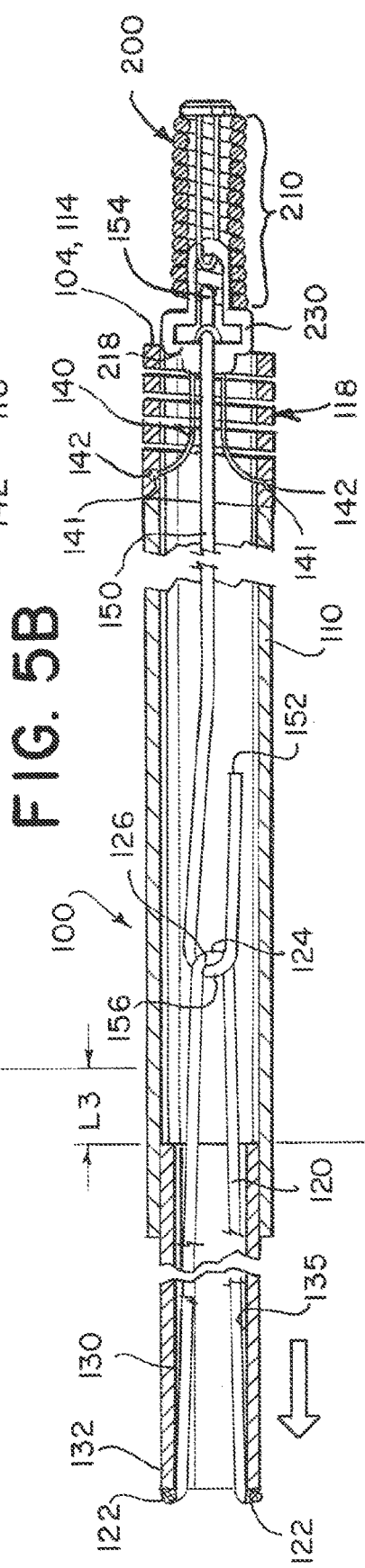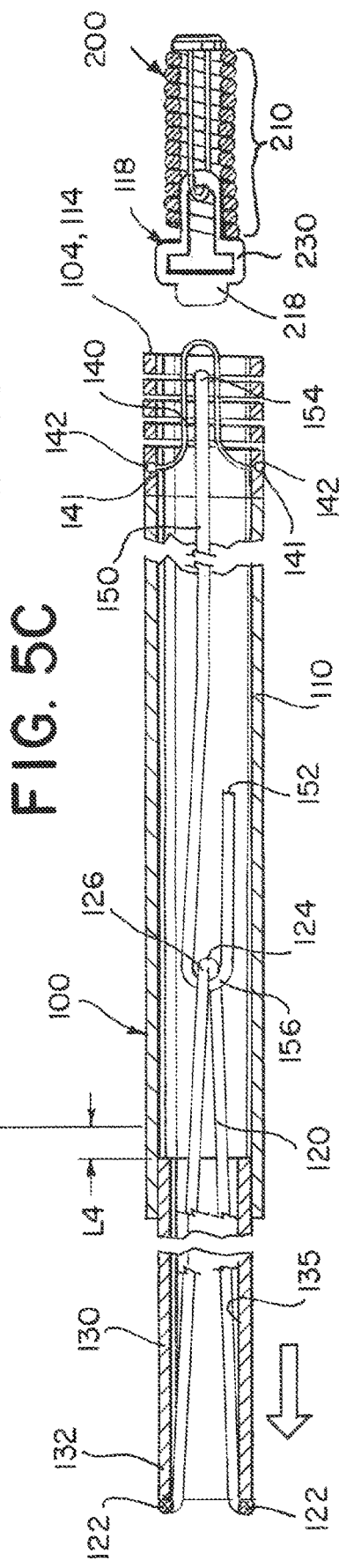

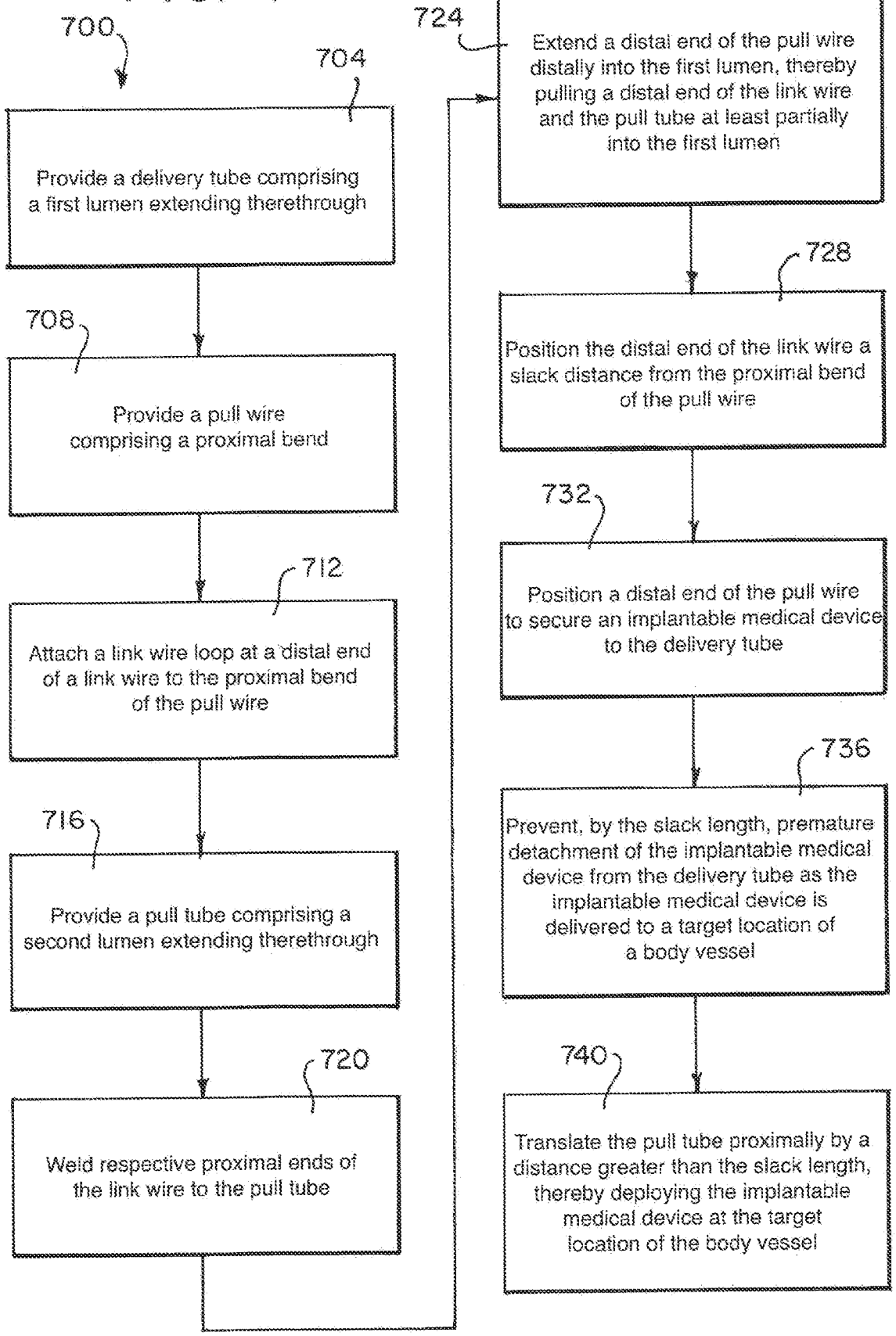

though the target location of the body vessel.

PROXIMAL LINK WIRE FOR PREVENTING PREMATURE IMPLANT DETACHMENT

FIELD OF INVENTION

The present invention relate to aneurysm treatment devices and more particularly, to improved delivery systems for embolic implants that prevent premature implant deployment.

BACKGROUND

Numerous intravascular implant devices are known in the field. Many are deployed mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire".

One issue with current catheter-based delivery systems is premature detachment of the implantable device. Premature detachment occurs when the implant is detached from the delivery system before reaching the treatment site. This may occur due to the tortuosity experienced by the delivery system as it passes through the vasculature of the patient, which can cause an increase in friction between the "pull wire" and the delivery system causing the pull wire to move proximally while the delivery system is moving distally.

Accordingly, there is a need for an improved implant delivery system that prevents premature detachment of the implant as it is delivered through tortuous vasculature. This disclosure is directed to this and other considerations.

SUMMARY

Various systems and methods of deploying an implant to a target location of a body vessel are disclosed. A delivery system can include a delivery tube and a pull tube, the pull tube at least partially disposed within a first lumen of the delivery tube. A link wire with two proximal ends can be welded to the pull tube and a distal end of the link wire can include a link wire loop. A pull wire can extend through the first lumen with a distal end positioned to secure the implant to the delivery system. The pull wire includes a proximal bend positioned around the link wire loop such that the proximal bend is positioned in a proximal direction relative to the distal end of the link wire loop by a slack length. The slack length is effective to prevent premature detachment of the implant from the delivery system.

In one aspect, a delivery system for deploying an implantable medical device to a target location of a body vessel is disclosed. The delivery system can include a delivery tube that includes a first lumen extending therethrough. The delivery system can include a pull tube that includes a second lumen extending therethrough. The pull tube can be at least partially disposed within the first lumen. The delivery system can include a link wire that includes two proximal ends welded to the pull tube. The link wire can be disposed at least partially within the second lumen and can include a distal end that includes a link wire loop. The delivery system can include a pull wire extending through the first lumen. The pull wire can include a distal end that is positioned to secure the implantable medical device to the delivery system. The pull wire can include a proximal bend that is positioned around the link wire loop such that the proximal bend is positioned in a proximal direction in relation to the distal end of the link wire loop by a slack length. The slack length can be effective to prevent premature detachment of the implantable medical device from the delivery system as the implantable medical device is delivered to the target location of the body vessel.

In some embodiments, the two proximal ends of the link wire can be welded to a proximal end of the pull tube. The distal end of the link wire can extend at least partially into the first lumen.

In some embodiments, the pull wire includes a free end positioned in a distal direction in relation to the distal end of the link wire loop.

In some embodiments, the delivery system can include a loop wire that includes a loop opening at a distal portion of the loop wire positioned approximate a distal end of the delivery tube and two loop wire attachment welds affixing respective loop wire proximal ends to a distal end of the delivery tube.

In some embodiments, the distal end of the delivery tube can include a compressed distal section. The loop wire can be effective to hold the compressed distal portion in compression while the implantable medical device is delivered to the target location of the body vessel. The compressed distal section can include a spiral-cut portion of the delivery tube. The compressed distal section can be configured to impart an elastic force to the implantable medical device when the implantable medical device is deployed to the target location of the body vessel.

In some embodiments, the implantable medical device can include a locking member and the loop opening can be positioned through the locking member, and the distal end of the pull wire can be positioned through the loop opening to thereby secure the implantable medical device to the delivery system.

In some embodiments, the pull wire can be coated with polytetrafluoroethylene (PTFE). In some embodiments, the slack length can be a distance greater than approximately 3 millimeters.

In some embodiments, the link wire can have a greater column strength than the pull wire.

In some embodiments, proximal translation of the pull tube is configured to cause the pull wire to translate proximally by a distance greater than the slack length to thereby deploy the implantable medical device to the target location of the body vessel.

In some embodiments, the implantable medical device can be an embolic coil.

In another aspect, a method is disclosed. The method can include providing a delivery tube that includes a first lumen extending therethrough. The method can include providing a pull wire that includes a proximal bend. The method can include attaching a link wire loop at a distal end of a link wire to the proximal bend of the pull wire such that the distal end of the link wire is positioned a slack length from the proximal bend of the pull wire. The method can include providing a pull tube including a second lumen extending therethrough and welding respective proximal ends of the link wire to the pull tube. The method can include extending a distal end of the pull wire distally into the first lumen to pull a distal end of the link wire and the pull tube at least partially into the first lumen. The method can include positioning a distal end of the pull wire to secure an implantable medical device to the delivery tube. The method can include preventing, by the slack length, premature detachment of the implantable medical device from the delivery tube as the implantable medical device is delivered to a target location of a body vessel. The method can include translating the pull wire proximally by a distance greater than the slack length to thereby deploy the implantable medical device at the target location of the body vessel.

In some embodiments, welding respective proximal ends of the link wire to the pull tube further includes welding respective proximal ends of the link wire to a proximal end of the pull tube such that the link wire is at least partially disposed within the second lumen.

In some embodiments, the method can include positioning a free end of the pull wire in a distal direction in relation to the distal end of the link wire loop.

In some embodiments, the distal end of the delivery tube can include a compressed distal section, and the compressed distal section can include a spiral-cut portion of the delivery tube. In some embodiments, securing the implantable medical device to the delivery tube can further include providing a loop wire that includes a loop opening at a distal portion of the loop wire and proximal ends of the loop wire. The method can include welding the proximal ends of the loop wire proximal to the compressed distal section. The method can include positioning the loop opening through a locking member of the implantable medical device and extending the distal end of the pull wire through the loop opening to secure the implantable medical device to the delivery tube.

In some embodiments, the method can include imparting, by the compressed distal section, an elastic force to the implantable medical device when the implantable medical device is deployed to the target location of the body vessel.

In some embodiments, the pull wire is coated with polytetrafluoroethylene (PTFE). In some embodiments, the slack length can be a distance greater than approximately 3 millimeters. In some embodiments, the link wire can have a greater column strength than the pull wire. In some embodiments, the implantable medical device can include an embolic coil.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 2 is an illustration of a delivery system navigating a body lumen according to aspects of the present invention.

FIGS. 3A-3C illustrates movement of a link wire as the delivery system is delivered through the body lumen of FIG. 2, according to aspects of the present invention.

FIGS. 5A-5C illustrates the movement of the pull tube that deploys the implant to a treatment site, according to aspects of the present invention.

FIG. 7 is a flowchart of an example method of using the delivery member, according to aspects of the present invention.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
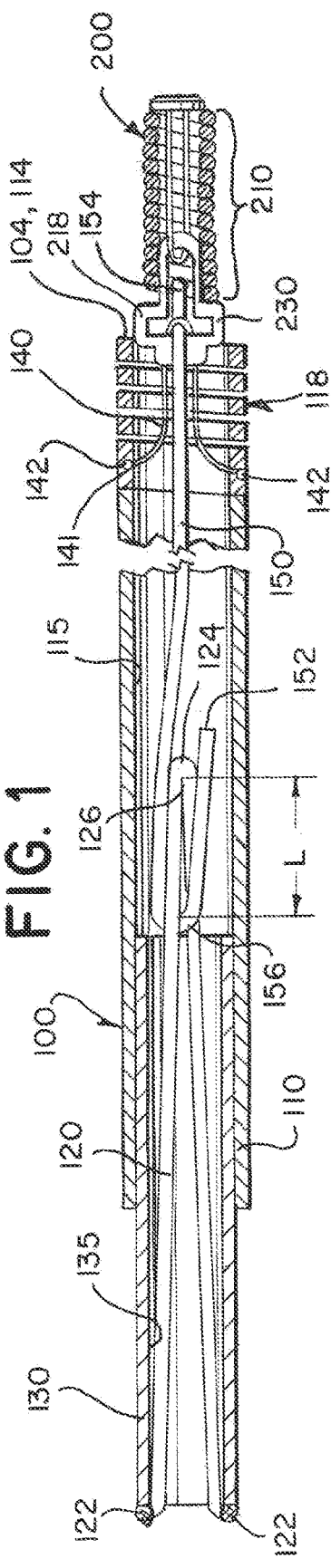
FIG. 1 an illustration of a delivery system and implant, according to aspects of the present invention.

Turning to the figures, FIG. 1 shows an example delivery system for deploying an implantable medical device 200 to a target location of a body vessel. The example delivery system can include a proximal tube 110. The proximal tube 110 can include a first lumen 115 extending therethrough. Disposed at least partially within the first lumen can be a pull tube 130. Pull tube 130 can include a second lumen 135 extending therethrough. Disposed within the second lumen of the pull tube can be a link wire 120. Link wire 120 can include two proximal ends that are attached to a proximal end 132 of the pull tube 130. Link wire 120 can also include a link wire loop 126 located at the distal end of the link wire. The link wire loop 126 can loop around a proximal bend 156 of a pull wire 150. The pull wire 150 can extend distally from the proximal bend 156 of pull wire 150 through the first lumen 115 and to a distal end 154 of the pull wire 150. The distal end 154 can extend to a distal end 104 of the delivery system 100. The distal end 154 of pull wire 150 can be secured through a loop wire opening 145 of a loop wire 140, which can secure an implant 200 to the delivery system 100. The pull wire can include a proximal free end 152 of pull wire 150, which can be located distal to the proximal bend 156 of pull wire 150. As shown in FIG. 1, the pull wire 150 can be in a "J" shaped hook configuration, with proximal free end 152 located distal to the proximal bend 156 of pull wire 150. A length measured between the link wire loop 126 and the proximal bend 156 of pull wire 150 can constitute slack length L. To deploy the implant 200 from the delivery system 100, pull tube 130 can be translated proximally, which reduces the slack length L until distal end of link wire 124 interfaces with the proximal bend 156 of pull wire 150. Further proximal movement of the pull tube 130 can be effective to deploy the implant 200 from the delivery system 100. Accordingly, slack length L can be effective to prevent premature detachment of an implant 200 from the delivery system 100 as delivery system 100 navigates tortuous vasculature of a patient as it delivers implant 200 to a treatment site. According to some embodiments, the slack length L may be a predetermined length that is effective to prevent premature detachment of implant 200 from delivery system 100. In some embodiments, the slack length L may measure more than approximately 3 millimeters.

Located proximate the distal end 104 of the delivery system 100 can be an implant 200. Implant 200 may be of any type known in the art, and in a preferred embodiment, the implant 200 may be an embolic coil. The implant 200 may include a microcoil 210 that is effective to treat aneurysms located at a distal end of the implant 200. At the proximal end of implant 200 can be a detachment feature 230. Detachment feature 230 can be provided as a proximal key that has a locking member 218 through which a loop wire opening 145 of loop wire 140 is positioned. After loop wire opening 145 is positioned through the locking member 218 of the detachment feature 230, the distal end 154 of pull wire 150 can be positioned through the loop wire opening 145 to secure the implant 200 to the delivery system 100. The loop wire 140 can additionally include loop wire proximal ends 141 that are attached to a distal portion of the proximal tube 110 by respective loop wire attachment welds 142. The loop wire attachment welds 142 can be placed just proximal to a compressible distal section 118 of the proximal tube 110. According to some embodiments, the compressed distal section 118 can be formed from a spiral-cut portion of the proximal tube 110, formed by a laser cutting operation. Additionally, or alternatively, the compressible portion can be formed of a wound wire, spiral ribbon, or other arrangement allowing axial adjustment according to the present invention. Preferably, compressible distal section 118 is in the elongated condition at rest and automatically or resiliently returns to the elongated condition from a compressed condition, unless otherwise constrained. In some embodiments, the loop wire 140 is effective to hold the compressed distal section 118 in compression while the implant 200 is delivered to the treatment site.

Pull wire 150 can be constructed out of any suitable material, for example, pull wire 140 can be constructed of stainless steel or memory shape material, such as nitinol. According to some embodiments, pull wire 150 can additionally be coated with polytetrafluoroethylene (PTFE). In some embodiments, the link wire 120 can have a greater column strength than the column strength of the pull wire 150. A link wire 120 with a greater column strength than the column strength of the pull wire ensures that the link 120 is not broken while a medical professional translates the pull tube 130 proximally to deploy the implant 200. Additionally, the dual welds 122 of the link wire 120 to the proximal end 132 of pull tube 130 increases the strength of securement of the proximal end of the delivery system 100 as compared to delivery systems that include only a single pull wire attached to the proximal end of a delivery system.

FIG. 2 illustrates positioning of an implant 200 such as an embolic coil suitable for aneurysm treatment, a guide catheter 300, and a delivery system 100 including a proximal tube 110 and a pull wire 150 within tortuous vasculature (vasculature not illustrated). At bends A, B, and C, the proximal tube 110 can extend to a sidewall of the guide catheter 300 on each outer curve of each bend, and likewise, the pull wire 150 can extend to a sidewall of the proximal tube 110 on each outer curve of each bend. During a procedure, the proximal tube 110 and pull wire 150 can be fed into the guide catheter 300 in the distal direction D, first passing through bend A, then bend B, and then bend C. As the proximal tube 110 and pull wire 150 navigate the bends, the pull tube 130 can translate proximally with respect to the proximal tube 110. The slack length L ensures that the proximal translation of the pull tube 130 with respect to the proximal tube 110 does not prematurely deploy implant 200 before implant 200 is delivered to the treatment site. As the pull tube 130 drifts proximally in relation to the proximal tube 110, the pull wire 150 remains stationary with respect to the proximal tube 110 as long as the pull tube 130 is translated by a distance less than the slack length L. Accordingly, the slack length L can be effective to prevent the premature detachment of implant 200 from the delivery system 100.

FIGS. 3A-3C illustrates movement of a link wire 120 as the delivery system is delivered through the body lumen of FIG. 2, according to aspects of the present invention. FIG. 3A shows the delivery system 100 after the delivery system 100 rounds bend A of FIG. 2. As shown in FIG. 3A, there remains a length L between the distal end 124 of the loop wire 120 and the proximal bend of pull wire 150 such that pull wire 150 is prevented from translating proximally due to proximal drift of the pull tube 130. FIG. 3B shows the delivery system 100 as the delivery system 100 rounds bend B of FIG. 2. As shown in FIG. 3B, the delivery tube 130 and link wire 120 drift proximally in relation to the proximal tube 110 by a distance of L1 due to navigating the tortuous vasculature of FIG. 2 as the delivery system 100 is navigated towards a treatment site. Because distance L1 is less than the slack length L, the pull wire 150 remains stationary with respect to the proximal tube 110 and the implant 200 is prevented from detaching prematurely. FIG. 3C shows the delivery system 100 as the delivery system 100 rounds bend C of FIG. 2. As shown in FIG. 3C, the delivery tube 130 and the link wire 120 drift have now drifted proximally in relation to the proximal tube 110 by a distance of L2 due to navigating the tortuous vasculature of FIG. 2 as the delivery system 100 is navigated towards the treatment site. Because distance L2 is less than the slack length L, the pull wire 150 remains stationary with respect to the proximal tube 110 and the implant 200 is prevented from detaching prematurely.

Figure 4:
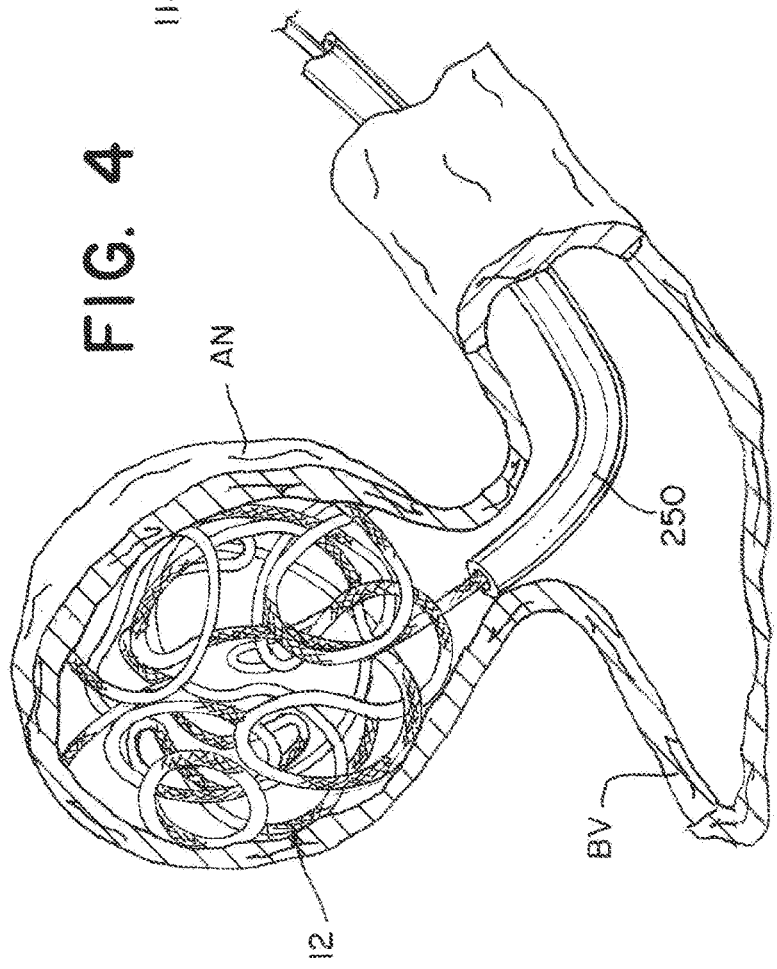
FIG. 4 is an illustration of embolic coils being positioned within an aneurysm according to aspects of the present invention.

FIG. 4 is an illustration of embolic implant 12 being delivered through catheter 250 and positioned within an aneurysm A on a blood vessel BV. The implant can loop and bend with the aneurysm sac to form a thrombotic mass. The implant can loop back on themselves and/or loop next to other implants. As the aneurysm A becomes increasingly packed, overlapping portions of the implant 12 can press into each other.

FIGS. 5A-5C illustrates the movement of the pull tube that deploys the implant to a treatment site, according to aspects of the present invention. FIG. 5A shows the configuration of the delivery system 100 after the delivery system has rounded bend C of FIG. 2 and approaches the treatment site as shown in FIG. 4. Once delivery system 100 is positioned such that implant 200 is approximate a treatment site, the delivery system 100 still has slack L3 between the distal end 124 of link wire 120 and the proximal bend 156 of pull wire. In order to deploy the implant 200, pull tube 130 can be translated proximally by a distance greater than the slack L3 left between the distal end 124 of link wire 120 and the proximal bend 156 of pull wire. The arrow in FIG. 5A indicates that a medical professional utilizing delivery system 100 can pull the pull tube 130 proximally to begin the deployment procedure of implant 200 from delivery system 100. In FIG. 5B, the pull tube 130 has been translated proximally by a distance of L3, thereby removing all the slack left in the delivery system 100 between the distal end 124 of link wire 120 and the proximal bend of pull wire 150. Accordingly, further proximal translation of the pull tube with respect to the proximal tube 110 is effective to deploy implant 200 from the delivery system 100. FIG. 5C shows the delivery system 100 just before the implant 200 is released from the delivery system 100. In FIG. 5C, the pull tube 130 is translated by an additional distance of L4. Because there is no slack left between the distal end of the loop wire 124 and the proximal bend 156 of the pull wire 150, any further proximal translation of the pull tube 130 is effective to translate the pull wire 150 proximally with respect to the proximal tube 110. That is, once the medical professional operating the delivery system 100 translates the pull tube 130 by a distance L4, the pull wire 150 translates together with pull tube 130 and link wire 120. As pull wire 150 is translated proximally, the distal end 154 of pull wire 150 exits loop opening 145 of loop 140, thereby allowing loop wire to exit from the detachment feature 230 of implant 200 and releasing implant 200 at the treatment site. The arrows in FIGS. 5A, 5B indicate the direction of proximal translation of the link wire. The arrows in FIG. 5C indicates that both the link wire 120 and the pull wire 150 are translated together to release implant 200 from delivery system 100.

Figure 6:
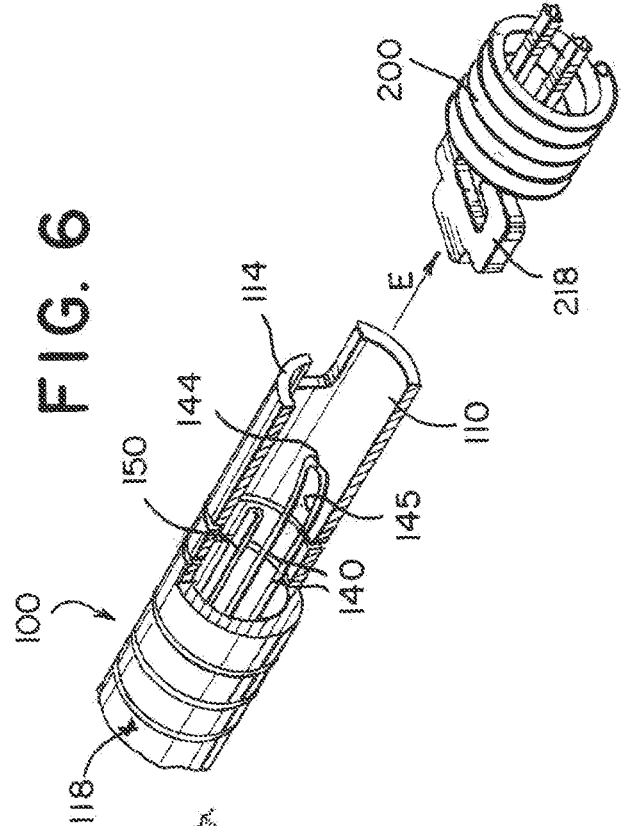
FIG. 6 illustrates the implant at the moment it is deployed from the delivery system, according to aspects of the present invention.

FIG. 6 illustrates the implant at the moment it is deployed from the delivery system, according to aspects of the present invention. As shown in FIG. 6, the implant 200 can be released from the delivery system 100 after the link wire 120 is translated proximally such that the pull wire 150 begins to translate proximally with link wire as a single unit. Here, the compressible distal section 118 has extended/returned to its original shape and "sprung" forward. An elastic force E is imparted by the distal end 114 of the proximal tube 100 to the medical device 200 to "push" it away to ensure a clean separation and delivery of the medical device 200.

The compressible distal portion 118 can have a difference in length (distance of compression) when measured in the compressed configuration and the original, uncompressed configuration of about 0.5 mm to about 0.75 mm. Greater elastic force E can be achieved by using a greater distance of compression. The distance of compression can be determined by the sizing of the loop wire 400, the shape of the locking member 218, and the shape of the distal end 114 of the proximal tube 110.

FIG. 7 is a flowchart of an example method of using the delivery system, according to aspects of the present invention. In block 704, the method can include providing a delivery tube 110. The delivery tube can include a first lumen 115 extending therethrough. In block 708, the method can include providing a pull wire 150 that includes a proximal bend 156. In block 712, the method can include attaching a link wire loop 126, located at a distal end 124 of the link wire 120, to the proximal bend 156 of the pull wire 150. In block 716, the method includes providing a pull tube 130. The pull tube includes a second lumen 135 extending therethrough. In block 720, the method includes welding respective proximal ends 122 of the link wire 120 to the pull tube 130 to attach the link wire to the pull tube 130. In block 724, the method can include extending a distal end 154 of the pull wire 150 distally into the first lumen, thereby pulling a distal end 124 of the link wire 120 at least partially into the first lumen 115. In block 728, the method can include positioning the distal end 124 of the link wire 120 a slack length L from the proximal bend 156 of the pull wire 150.

In block 732, the method can include positioning a distal end 154 of the pull wire to secure an implantable medical device 200 to the delivery tube 110. In block 736, the method can include preventing, by the slack length L, premature detachment of the implantable medical device 200 from the delivery tube 110 as the implantable medical device is delivered to a target location of a body vessel. In block 740, the method can include translating the pull tube proximally by a distance greater than the slack length L to thereby deploy the implantable medical device 200 at the target location of the body vessel.

According to some embodiments, welding respective proximal ends 122 of the link wire 120 to the pull tube 130 further includes welding respective proximal ends 122 of the link wire 120 to a proximal end 132 of the pull tube 130 such that the link wire 120 is at least partially disposed within the second lumen 135.

According to some embodiments, the method can include positioning a free end 152 of the pull wire 150 in a distal direction in relation to the distal end 124 of the link wire loop 126.

According to some embodiments, a distal end 114 of the delivery tube 110 includes a compressed distal section 118. The compressed distal section 118 can include a spiral-cut portion of the delivery tube 110. Securing the implantable medical device 200 to the delivery tube 110 can further include providing a loop wire that includes a loop opening at a distal portion 144 of the loop wire and proximal ends 141 of the loop wire, welding 142 the proximal ends 141 of the loop wire proximal to the compressed distal section 118, positioning the loop opening 145 through a locking member 218 of the implantable medical device 200, and extending a distal end 154 of the pull wire 150 through the loop opening 145 to secure the implantable medical device 200 to the delivery tube 110.

According to some embodiments, the method can include imparting, by the compressed distal section 118, an elastic force E to the implantable medical device 200 when the implantable medical device 200 is deployed to the target location of the body vessel.

According to some embodiments, the pull wire 140 can be coated with polytetrafluoroethylene. In some embodiments, the slack length L can be a distance greater than approximately 3 millimeters. In some embodiments, the link wire 120 has a greater column strength than the pull wire 140. In some embodiments, the implantable medical device can be an embolic coil.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. Modifications apparent to those skilled in the pertinent art are intended to be within the scope of the claims which follow.

The invention claimed is:

1. A delivery system for deploying an implantable medical device to a target location of a body vessel, the delivery system comprising:
   a delivery tube comprising a first lumen extending therethrough;
   a pull tube comprising a second lumen extending therethrough, the pull tube at least partially disposed within the first lumen;
   a link wire comprising two proximal ends welded to the pull tube, the link wire disposed at least partially within the second lumen and a distal end comprising a link wire loop; and
   a pull wire extending through the first lumen, the pull wire comprising a distal end that is positioned to secure the implantable medical device to the delivery system and a proximal bend positioned around the link wire loop such that the proximal bend is positioned in a proximal direction in relation to the distal end with the link wire loop by a slack length,
   wherein the slack length is effective to prevent premature detachment of the implantable medical device from the delivery system as the implantable medical device is delivered to the target location of the body vessel.

2. The delivery system of claim 1,
   wherein the two proximal ends of the link wire are welded to a proximal end of the pull tube, and
   wherein the distal end of the link wire extends at least partially into the first lumen.

3. The delivery system of claim 1, wherein the pull wire comprises a free end positioned in a distal direction in relation to the distal end with the link wire loop.

4. The delivery system of claim 1, further comprising:
   a loop wire comprising:
      a loop opening at a distal portion of the loop wire positioned approximate a distal end of the delivery tube; and
      two loop wire attachment welds affixing respective loop wire proximal ends to the distal end of the delivery tube.

5. The delivery system of claim 4,
   wherein the distal end of the delivery tube comprises a compressed distal section, wherein the loop wire is effective to hold the compressed distal section in compression while the implantable medical device is delivered to the target location of the body vessel,
   wherein the compressed distal section comprises a spiral-cut portion of the delivery tube, and
   wherein the compressed distal section is configured to impart an elastic force to the implantable medical device when the implantable medical device is deployed to the target location of the body vessel.

6. The delivery system of claim 4, the implantable medical device comprising a locking member, wherein the loop opening is configured to be positioned through the locking member, and the distal end of the pull wire is positioned through the loop opening, thereby securing the implantable medical device to the delivery system.

7. The delivery system of claim 1, wherein the pull wire is coated with polytetrafluoroethylene (PTFE).

8. The delivery system of claim 1, wherein the slack length is a distance greater than approximately 3 millimeters.

9. The delivery system of claim 1, the link wire having a greater column strength than the pull wire.

10. The delivery system of claim 1, wherein proximal translation of the pull tube is configured to cause the pull wire to translate proximally by a distance greater than the slack length, thereby deploying the implantable medical device to the target location of the body vessel.

11. The delivery system of claim 1, wherein the implantable medical device comprises an embolic coil.

12. A method, comprising:
   providing a delivery tube comprising a first lumen extending therethrough;
   providing a pull wire comprising a proximal bend;
   attaching a link wire loop at a distal end of a link wire to the proximal bend of the pull wire;
   providing a pull tube comprising a second lumen extending therethrough;
   welding respective proximal ends of the link wire to the pull tube;
   extending a distal end of the pull wire distally into the first lumen, thereby pulling the pull tube and a distal end of the link wire at least partially into the first lumen;
   positioning the distal end of the link wire a slack length from the proximal bend of the pull wire;
   positioning the distal end of the pull wire to secure an implantable medical device to the delivery tube;
   preventing, by the slack length, premature detachment of the implantable medical device from the delivery tube as the implantable medical device is delivered to a target location of a body vessel; and
   translating the pull tube proximally by a distance greater than the slack length, thereby deploying the implantable medical device at the target location of the body vessel.

13. The method of claim 12, wherein welding respective proximal ends of the link wire to the pull tube further comprises welding respective proximal ends of the link wire to a proximal end of the pull tube such that the link wire is at least partially disposed within the second lumen.

14. The method of claim 12, further comprising:
   positioning a free end of the pull wire in a distal direction in relation to the distal end of the link wire loop.

15. The method of claim 12,
   wherein a distal end of the delivery tube comprises a compressed distal section,
   wherein the compressed distal section comprises a spiral-cut portion of the delivery tube, and
   wherein securing the implantable medical device to the delivery tube further comprises:
      providing a loop wire comprising a loop opening at a distal portion of the loop wire and proximal ends of the loop wire;
      welding the proximal ends of the loop wire proximal to the compressed distal section;
      positioning the loop opening through a locking member of the implantable medical device; and
      extending the distal end of the pull wire through the loop opening to secure the implantable medical device to the delivery tube.

16. The method of claim 15, further comprising imparting, by the compressed distal section, an elastic force to the implantable medical device when the implantable medical device is deployed to the target location of the body vessel.

17. The method of claim 12, further comprising coating the pull wire with polytetrafluoroethylene (PTFE).

18. The method of claim 12, wherein the slack length is a distance greater than approximately 3 millimeters.

19. The method of claim 12, wherein the link wire has a greater column strength than the pull wire.

20. The method of claim 12, wherein the implantable medical device comprises an embolic coil.

* * * * *